(12) United States Patent
Saito et al.

(10) Patent No.: US 6,555,701 B2
(45) Date of Patent: Apr. 29, 2003

(54) CVD MATERIAL COMPOUND AND METHOD FOR MANUFACTURING THE SAME AND CVD METHOD OF RUTHENIUM OR RUTHENIUM COMPOUND THIN FILM

(75) Inventors: Masayuki Saito, Kanagawa (JP); Junichi Taniuchi, Kanagawa (JP); Koji Okamoto, Kanagawa (JP); Hiroaki Suzuki, Kanagawa (JP)

(73) Assignee: Tanaka Kikinzoku Kogyo K.K., Tokyo (JP)

( * ) Notice: Subject to any disclaimer, the term of this patent is extended or adjusted under 35 U.S.C. 154(b) by 0 days.

(21) Appl. No.: 10/175,873

(22) Filed: Jun. 21, 2002

(65) Prior Publication Data
US 2003/0054638 A1 Mar. 20, 2003

(30) Foreign Application Priority Data

Aug. 10, 2001 (JP) ........................................ 2001-243927

(51) Int. Cl.$^7$ ............................. C07F 15/00; C23C 8/00
(52) U.S. Cl. ........................ 556/40; 556/136; 427/585; 427/587; 427/250; 427/255.31
(58) Field of Search ................... 556/40, 136; 427/585, 427/587, 250, 255.31

(56) References Cited

U.S. PATENT DOCUMENTS 6,316,064 B1 * 11/2001 Onozawa et al. ........... 427/585

FOREIGN PATENT DOCUMENTS

JP          06-283438         * 10/1994

* cited by examiner

*Primary Examiner*—Porfirio Nazario-Gonzalez
(74) *Attorney, Agent, or Firm*—Rothwell, Figg, Ernst & Manbeck

(57) ABSTRACT

The present invention provides a CVD material compound based on an organic ruthenium compound, the organic ruthenium compound consisting of one of cis and trans isomers of tris (2,4-octa-dionato) ruthenium (III). The organic ruthenium compound which consists of cis or trans isomer can be isolated by the steps of preparing tris (2,4-octa-dionato) ruthenium (III) in any method, making the tris (2,4-octa-dionato) ruthenium (III) adsorbed on an adsorbent including alumina, bringing the adsorbent into contact with a first solvent to elute the trans isomer and then bringing the adsorbent into contact with a second solvent having a polarity higher than that of the first solvent to elute the cis isomer.

4 Claims, 4 Drawing Sheets cis-tris (2,4-octa-dionato) ruthenium (III)

Ru

O  O trans-tris (2,4-octa-dionato) ruthenium (III)

Ru

O  O

CVD MATERIAL COMPOUND AND METHOD FOR MANUFACTURING THE SAME AND CVD METHOD OF RUTHENIUM OR RUTHENIUM COMPOUND THIN FILM

BACKGROUND OF THE INVENTION

1. Field of the Invention

The present invention relates to a CVD material for forming a ruthenium or ruthenium compound thin film.

2. Description of the Related Art

Recently, thin film electrodes made of ruthenium or ruthenium oxides are investigated for use in semiconductor devices such as Dynamic RAMs (DRAMs). These materials have lower resistivities which can provide excellent electric properties of the electrodes. They are investigated for use in the storage electrodes in capacitors for DRAMs. The materials are expected to significantly contribute to high density DRAMs. The ruthenium thin films draw attentions as one of major materials for the thin film electrodes.

The ruthenium or ruthenium thin films are often formed by the sputtering method as well as the chemical vapor deposition (hereinafter referred to as CVD) method. The CVD method can easily provide thin films of more uniformity and particularly higher step coverage than those by the sputtering method. Thus, the CVD method is expected to become a major process for manufacturing thin film electrodes which can provide recent circuits and electronic components of much higher density.

The CVD material for forming ruthenium and ruthenium compound thin films requires properties generally including a lower melting point and a higher vapor pressure. One of the recently proposed CVD methods is a solution CVD in which the material organic compound is not directly evaporated but is dissolved in a solvent such as an organic solvent which is then vaporized. The solution CVD is effective for a material organometallic compound of a higher melting point but the solution CVD requires a material to be soluble in the organic solvent.

Recent investigations on organic ruthenium compounds which have the above properties have proposed various organic ruthenium compounds. One of the compounds is described in Japanese Patent Application Laid-Open No. 2000-212744 which discloses β-diketonato-ruthenium expressed by the following formula.

[Formula 1]

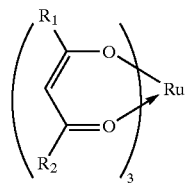

where, R1 and R2 represent different alkyls having 1 to 4 carbon atoms.

The above organic ruthenium compound comprises a ruthenium metal coordinated with β-diketone. The compound has a lower melting point and exists in liquid states at room temperature and also has higher solubility and stability in organic solvents. Thus, the compound itself can be handled easily as CVD material and also serve as a suitable material for the solution CVD.

However the inventors found out that the above described ruthenium compound may produce ruthenium thin films by CVD process which can have relatively easy handling and high purity but poor morphology, particularly high surface roughness.

The surface roughness is very small on the order of nanometer which can, however, have a large impact on thin film electrodes. In addition, recent semiconductor devices have been required to have higher performances, and particularly research works on DRAMs aim to increase their capacitance from Mbit to Gbit size. For those purposes, the devices should essentially have very high densities so that thin film electrodes need to have morphology with very high precision.

The present invention is made under the above described background. It is an object of the present invention to provide a CVD material compound based on an organic ruthenium compound, which has a lower melting temperature, higher solubility in solvent and capability of forming a good morphology thin film, and a method for manufacturing the material compound.

SUMMARY OF THE INVENTION

To solve the above mentioned problems, the inventors have paid attention to tris (2,4-octa-dionato) ruthenium which is one of the β-diketonato ruthenium as expressed by the formula 2. Tris (2,4-octa-dionato) ruthenium is also found to show poor thin film morphology. The investigations of the morphology have shown that tris (2,4-octa-dionato) ruthenium has two geometrical isomers, cis and trans isomers as shown in FIG. 1 and the known manufacturing methods produce tris (2,4-octa-dionato) ruthenium which consists of the two geometrical isomers. It has also been shown that mixed isomers of tris (2,4-octa-dionato) ruthenium can not form thin films having good step coverage.

The different geometrical isomers have the same molecular formula and very different physical properties. As regards the properties of the CVD materials, the different geometrical isomers are considered to have different evaporation and decomposition rates. Thus mixed geometrical isomers of the compounds cannot form thin films at a constant deposition rate during the CVD process and may degrade the thin film morphology. It has not been disclosed how the thin film morphology is affected by the CVD process which uses mixed isomers of an organic metal compound. The inventors have recognized that the CVD material requires such properties that it has high purity and does not have mixed isomers but has one of the isolated isomers. The recognition has led the inventors to the present invention.

The present invention provides a CVD material compound based on an organic ruthenium compound, the organic ruthenium compound consisting only of one of cis and trans isomers of tris (2,4-octa-dionato) ruthenium (III) as expressed by the following formula.

[Formula 2]

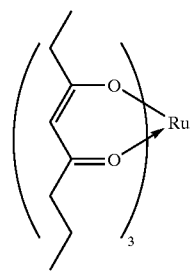

According to the present invention, the geometrical isomers are isolated and only the cis or trans isomer can be the main ingredient so that the evaporation, decomposition, and deposition rates can be kept constant. According to the present invention, the preferable ruthenium compound is the trans geometrical isomer which can form thin films of smaller surface roughnesses and better morphology.

According to the present invention, mixed geometrical isomers tris (2,4-octa-dionato) ruthenium are separated into the cis and trans isomers each of which is used independently as a CVD material. The cis and trans isomers have different dipole moments. The trans isomer can have a smaller dipole moment in the complex molecular which may provide a lower adsorption on the adsorbent such as an alumina. Since the dipole moment results from the vector sum of the bond moments, the cis isomer can have a dipole moment larger than that of the trans isomer which may provide a higher adsorption on the adsorbent. According to the present invention, the above natures are used to isolate the geometrical isomers of tris (2,4-octa-dionato) ruthenium. Specifically, the alumina adsorbent adsorbs mixed geometrical isomers of tris (2,4-octa-dionato) ruthenium. Then a solvent is passed through the adsorbent to first elute the trans isomer which has a smaller dipole moment (or lower adsorbability). Then another solvent having a polarity higher than that of the first solvent is passed through the adsorbent to elute the cis isomer. Thus, both isomers are isolated to be used as CVD materials.

In other words, a method for producing a CVD material compound according to the present invention comprises the steps of preparing tris (2,4-octa-dionato) ruthenium (III), adsorbing the tris (2,4-octa-dionato) ruthenium (III) on an adsorbent including alumina, and contacting the adsorbent with a first solvent to elute the trans isomer and then contacting the adsorbent with a second solvent having a polarity higher than that of the first solvent to elute the cis isomer.

The first and second solvents should basically be selected to have different polarities. In general, nonpolar solvents include hexane, cyclohexane, benzene etc., and the polar solvents include alcohol, acetone, ethyl acetate etc. According to the present invention, the above compounds can be used either alone or in combination. For example, as the first solvent can be used one of the above nonpolar solvents alone, and as the second solvent can be used one of the above polar solvents alone. Alternatively, as the first and second solvents can be used in nonpolar and polar solvents different mixtures. The solvents are mixed to provide different polarities for each mixture. As a specific example, as the first and second solvents can be used hexane (nonpolar solvent) and ethyl acetate (polar solvent) in solvent mixture. The mixing ratio of each mixed solvent is set at different values.

Tris (2,4-octa-dionato) ruthenium is preferably separated into two geometrical isomers via liquid chromatography. As adsorbents can be preferably used the alumina for use in chromatography, that is to say, an activated alumina.

Tris (2,4-octa-dionato) ruthenium (or a mixture of its geometrical isomers) to be separated can be prepared by the reaction between 2,4-octadione and ruthenium compounds such as ruthenium chloride and ruthenium nitrate.

Lastly, the method for forming thin films with CVD material based on cis and trans-tris (2,4-octa-dionato) ruthenium according to the present invention will be described. The thin film formation method is basically the same as the general CVD method. That is to say, the CVD material compound is evaporated and transported onto the substrate surface where the compound is decomposed to deposit ruthenium or ruthenium compound thereon. The CVD material according to the present invention can be liquid at room temperature and also highly soluble in an organic solvent. Thus, during evaporation of the CVD material, the CVD material can directly be heated, or alternatively the CVD material according to the present can be dissolved in the organic solvent which is in turn heated by the solution CVD. Both methods are effective for the deposition. In the solution CVD, the CVD material can be dissolved in various organic solvents including alcohols such as methanol and ethanol. During evaporation of the CVD material, the CVD material can directly be heated to a temperature between 150 and 200° C., and the CVD material solution according to the solution CVD can preferably be heated to a temperature between 150 and 200° C., depending on the organic solvent in which the CVD material is dissolved.

The CVD material molecules which are evaporated and transported onto the substrate surface can be decomposed in any method including thermal CVD and plasma CVD. In particular, the thermal CVD is preferable because it can use a simpler apparatus and the CVD material according to the present invention can be decomposed at relatively low temperatures which can provide little risk of damaged wafers. In the thermal CVD, the substrate temperature can preferably be of 250° C. to 400 ° C. for the decomposition of the ruthenium compound.

The thermal CVD process can preferably be performed in a reactor at a reduced pressure. Reduced pressure can improve the thin film thickness uniformity and the step coverage. The reactor can preferably have the pressure of 13 to 700 Pa.

DETAILED DESCRIPTION OF THE PREFERRED EMBODIMENTS

Figure 1:
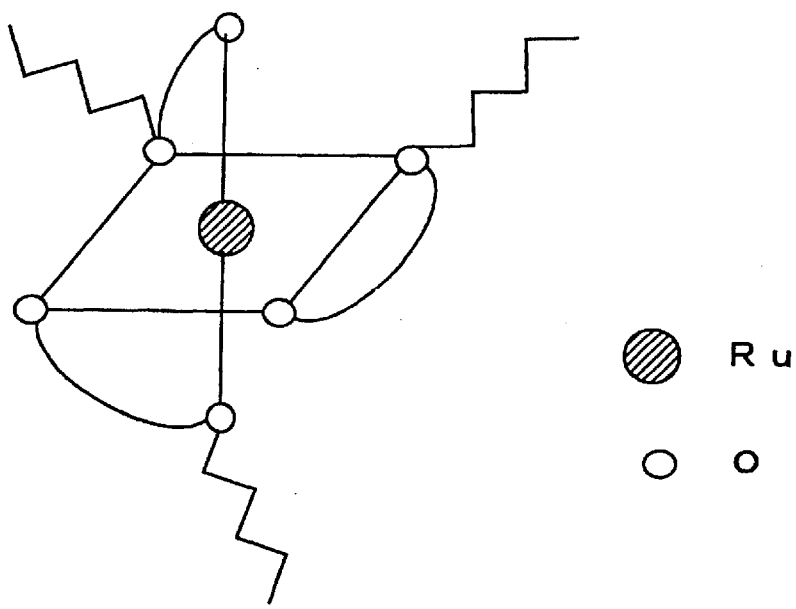
FIG. 1 shows a graphical formula of the cis and trans geometrical isomers of tris (2,4-octa-dionato) ruthenium according to the present invention.
Figure 1:
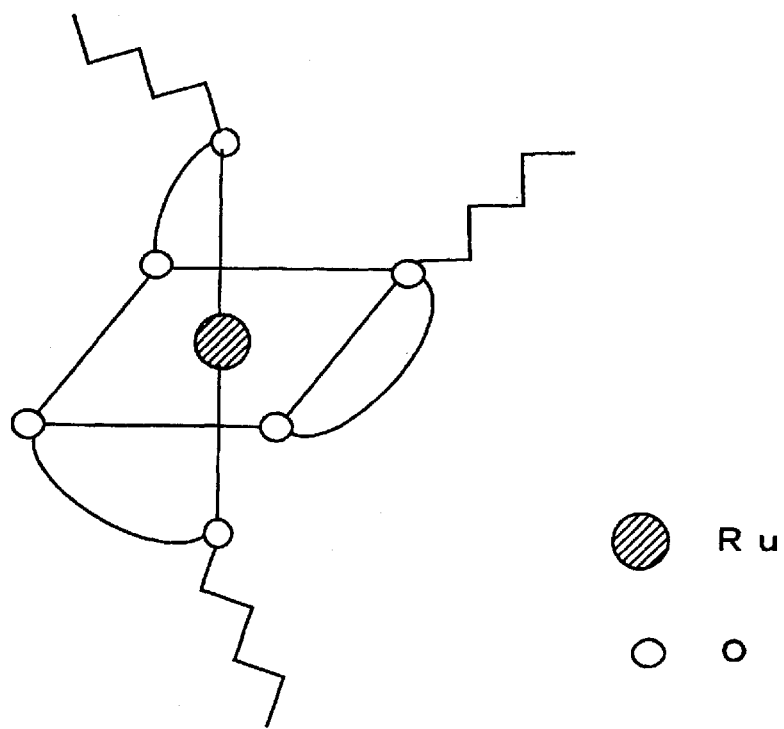
Figure 2:
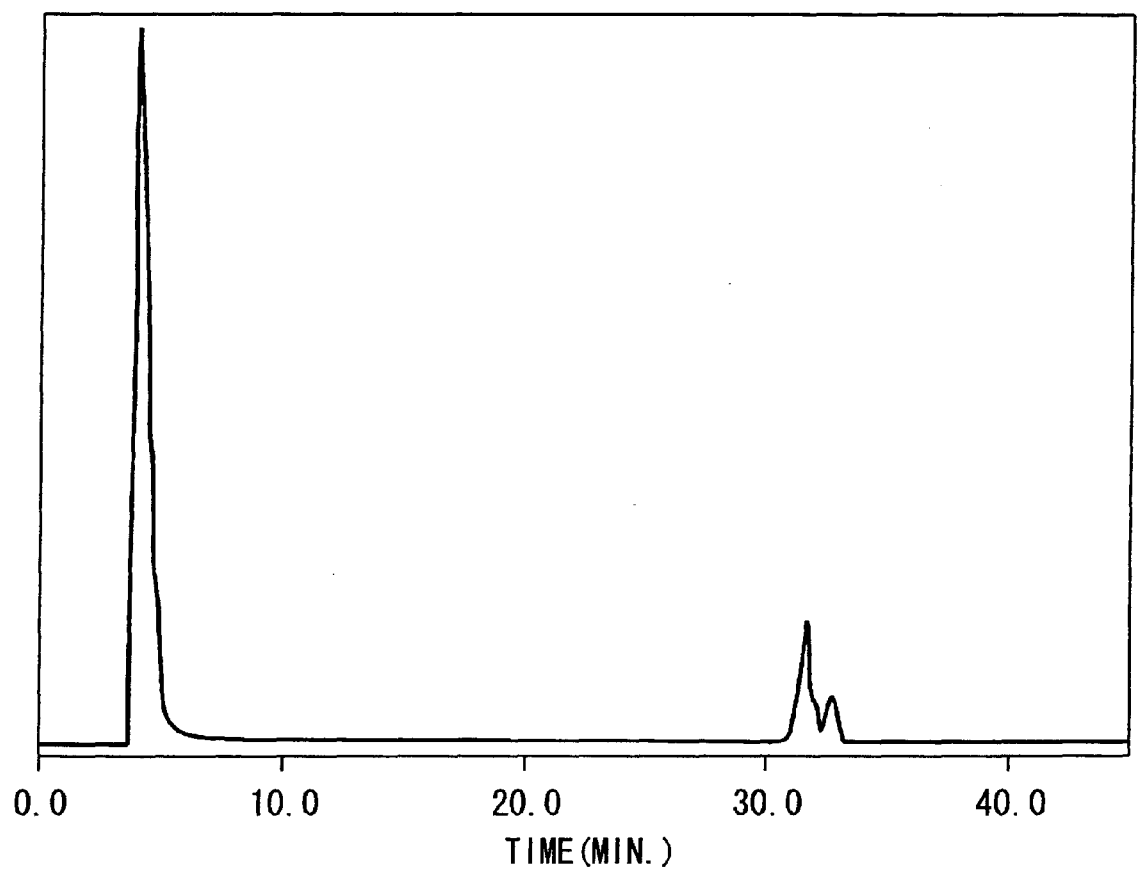
FIG. 2 shows a gas chromatography profile of the unseparated tris (2,4-octa-dionato) ruthenium (III) prepared according to the present invention.

Preferred embodiments of the present invention will be described with reference to the accompanying drawings.
First Embodiment To the ethanol solvent were added 206 g of ruthenium chloride and 500 g of 2,4-octadione and mixed. To the mixture was then added 100 g of sodium carbonate for neutralization reaction. The reaction liquid was then extracted with benzene and the solvent was evaporated. Thus, 600 g of tris (2,4-octa-dionato) ruthenium (III) being red was obtained. FIG. 2 shows a gas chromatography profile of the resultant tris (2,4-octa-dionato) ruthenium (III). FIG. 2 shows that tris (2,4-octa-dionato) ruthenium (III) prepared according to the present invention has two peaks. The peak at lower time side indicates the trans isomer and the peak at higher time side indicates the cis isomer. Tris (2,4-octa-dionato) ruthenium (III) had a mixing ratio of trans isomer 75% and cis isomer 25%. Tris (2,4-octa-dionato) ruthenium (III) is liquid at room temperature.

Figure 3:
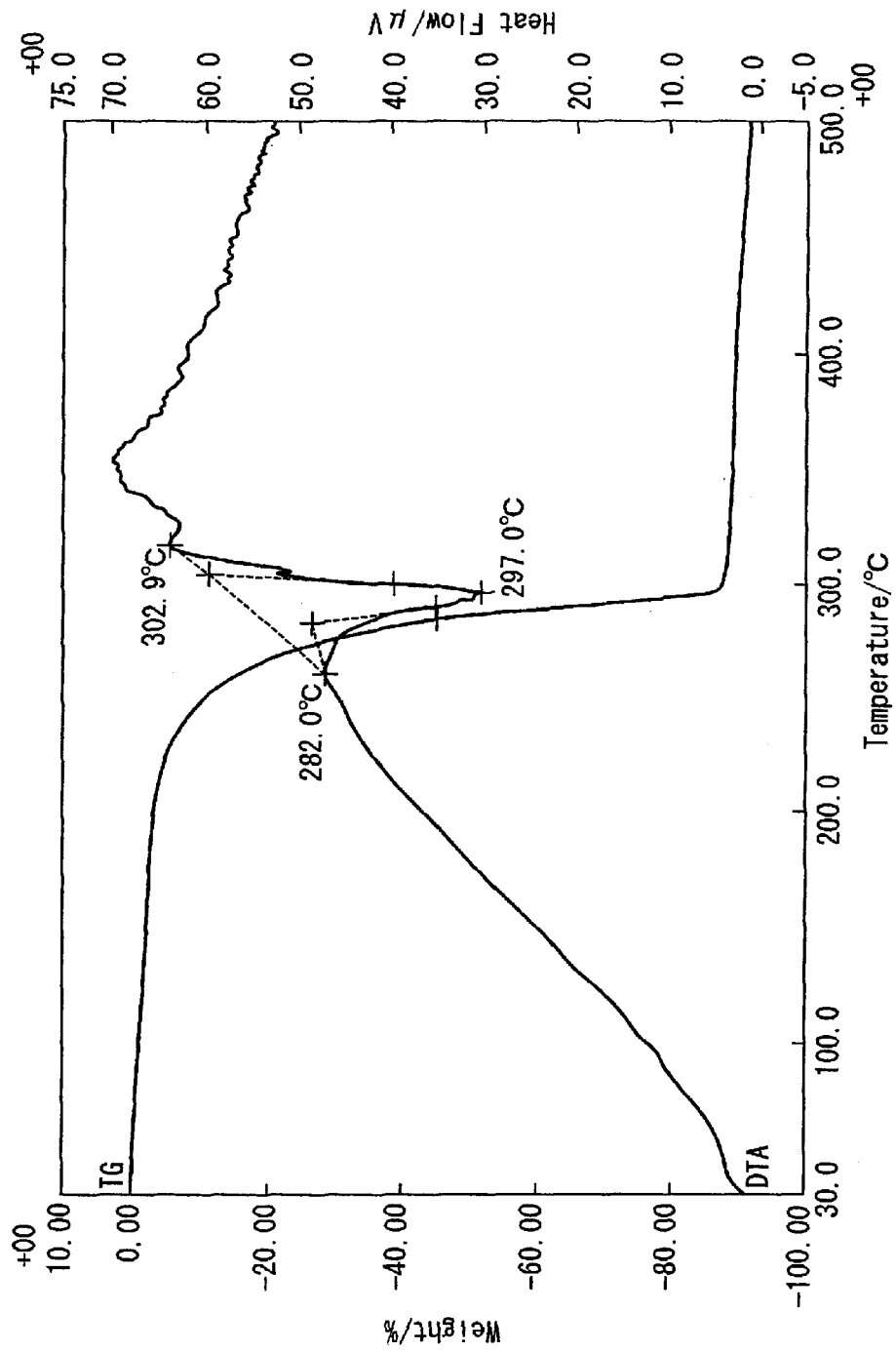
FIG. 3 shows a TG-DTA curves of trans-tris (2,4-octa-dionato) ruthenium (III) according to the present invention.
Figure 4:
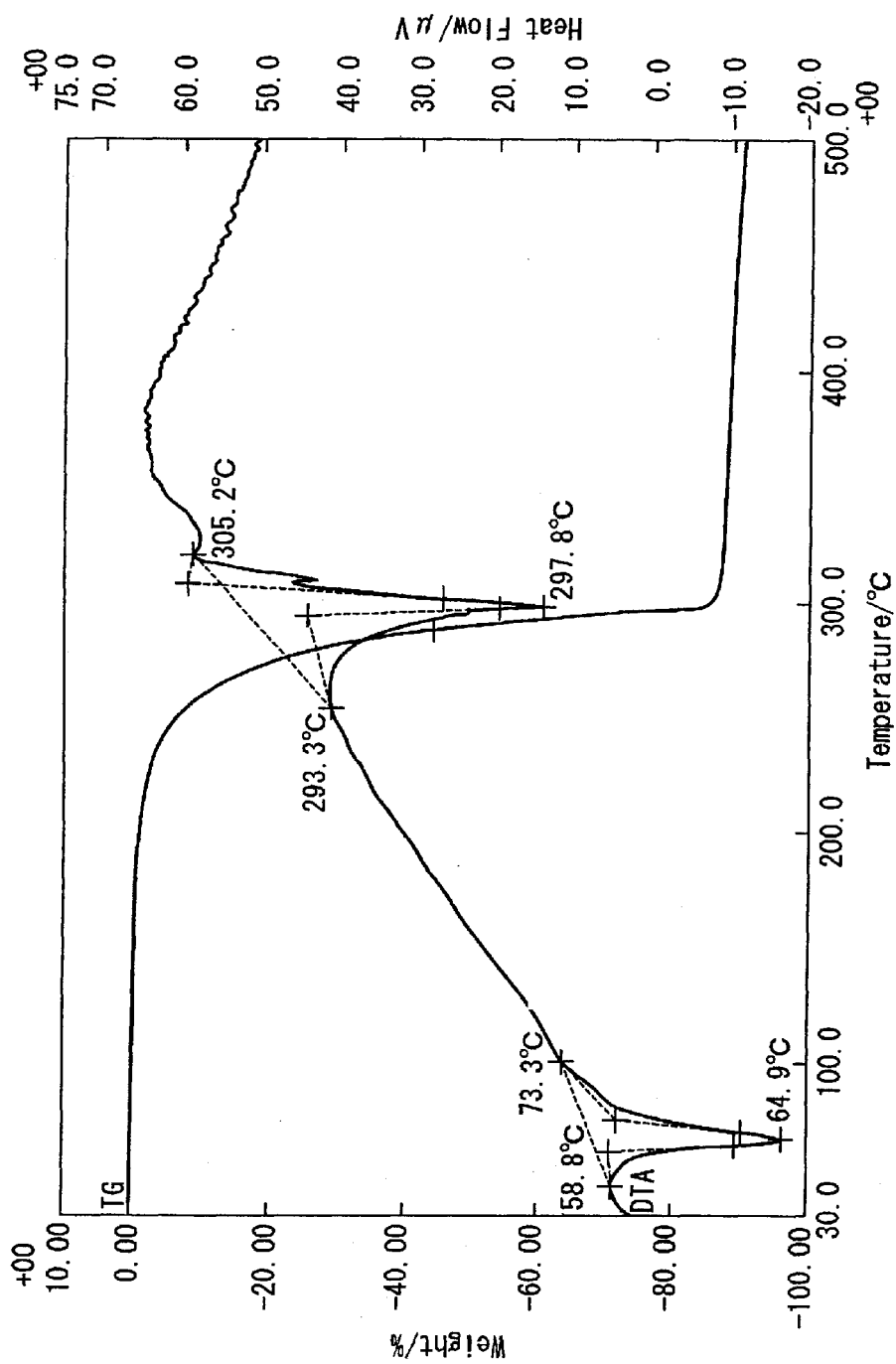
FIG. 4 shows a TG-DTA curves of cis-tris (2,4-octa-dionato) ruthenium (III) according to the present invention.

Tris (2,4-octa-dionato) ruthenium (III) was then separated into two geometrical isomers. The separation was performed by liquid chromatography with the use of alumina in the column. Tris (2,4-octa-dionato) ruthenium (III) prepared was passed through the alumina column and adsorbed thereon. The solution mixture of hexane/ethyl acetate (mixing ratio 9:1) was then passed through the column to first isolate the trans isomer. Additional solution mixture of hexane/ethyl acetate (mixing ratio 1:1) was then passed through the adsorbent from which the trans isomer had been isolated, to elute the cis isomer. The trans and cis isomers thus isolated of tris (2,4-octa-dionato) ruthenium (III) were both subjected to the thermogravimetry differential thermal analysis (TG-DTA). FIGS. 3 and 4 show the analysis results for trans and cis isomers respectively. Those results show that the trans-tris (2,4-octa-dionato) ruthenium (III) is liquid at room temperature and the cis-tris (2,4-octa-dionato) ruthenium (III) is solid at room temperature.

Isolated cis and trans-tris (2,4-octa-dionato) ruthenium (III) were used independently as CVD material for depositing the ruthenium thin films. A general CVD method was used here in which the materials are bubbled with a bubbler and simultaneously directly heated (this method is referred to as bubbler method hereinafter). The deposition conditions are as follows.

CVD materials heating temperature (bubbler temperature): 150° C.

Carrier gas flow rate: 90 sccm

Reactor pressure: 533 Pa (4 torr)

Substrate temperature: 350° C.

The morphology of the resultant thin film was investigated with Atomic Force Microscopy (AFM). The AFM shows that the surface roughness is $R_{MS}$=2.1 nm for the trans thin film and $R_{MS}$=4.2 nm for the cis thin film.

Second Embodiment

In this embodiment, the ruthenium thin film was formed through a solution CVD method in which the cis and trans-tris (2,4-octa-dionato) ruthenium (III) prepared in the first embodiment was used as materials to be dissolved in a solvent which was then heated in an evaporator (this method is referred to as evaporator method hereinafter). Ethanol was used as the solvent to dissolve the materials. The deposition was performed under the following conditions.

Solution heating temperature (heater temperature): 200° C.

Carrier gas flow rate: 90 sccm

Reactor pressure: 1066 Pa (8 torr)

Substrate temperature: 350° C.

The morphology of the resultant thin film was investigated with AFM as in the first embodiment. The AFM shows that the surface roughness is $R_{MS}$=1.0 nm for the trans thin film and $R_{MS}$=1.5 nm for the cis thin film.

COMPARATIVE EXAMPLE

For comparison with the above two embodiments, tris (2,4-octa-dionato) ruthenium (III) prepared in the first embodiment was used in a mixture of the isomers without separation to form the ruthenium thin films. The thin films were formed through the bubbler method and evaporator method as in the first and second embodiments. The deposition conditions were the same as in the first and second embodiments.

In the deposition process of the comparative example, in the bubbler method, formation of the thin films were not confirmed during the initial introduction of the CVD materials, but were confirmed finally after a while. In the evaporator method, formation of the films was confirmed with a low deposition rate and later with increased rates. Thus, either method did not provide a constant deposition rate for the materials of mixed geometrical isomers according to the comparative example.

The morphology of the resultant thin film was investigated with AFM as in the first and second embodiments. The AFM shows that the surface roughness is $R_{MS}$=14.3 nm for the thin film prepared by the bubbler method of CVD, and $R_{MS}$=4.2 to 10.5 nm for the thin film by the evaporator method of CVD. Thus both thin films are nonuniform.

The surface roughnesses of the ruthenium thin films prepared in the first and second embodiments and the comparative example are summarized in Table 1.

TABLE 1

|  |  |  | $R_{MS}$ | Deposition rate |
|---|---|---|---|---|
| Bubbler method | First embodiment | Trans isomer | 2.1 nm | Constant |
|  |  | Cis isomer | 4.2 nm | Constant |
|  | Comparative example | Mixture | 14.3 nm | Not constant |
| Evaporator method | Second embodiment | Trans isomer | 1.0 nm | Constant |
|  |  | Cis isomer | 1.5 nm | Constant |
|  | Comparative example | Mixture | 4.2–10.5 nm | Not constant |

Table 1 shows that the CVD materials of both cis and trans isomers according to the first and second embodiments can provide thin films which have lower surface roughness and better morphology than the CVD materials of mixed cis and trans isomers. This tendency can be true in both the bubbler and evaporator methods. Thus the CVD materials according to the present invention can provide good morphology thin films through both methods.

Further, the CVD materials according to the first and second embodiments can provide a constant deposition rate from the initial stage of the deposition. The CVD materials according to the comparative example tend to provide a deposition rate which is low in the initial stage of the deposition (zero rate for the bubbler method) and increases later. This is considered due to the mixed cis and trans isomers which provide different evaporation and decomposition rates.

What is claimed is:

1. A CVD material compound based on an organic ruthenium compound, wherein said organic ruthenium compound consists of one of cis and trans isomers of tris (2,4-octa-dionato) ruthenium (III) as expressed by the following formula

[Formula 3]

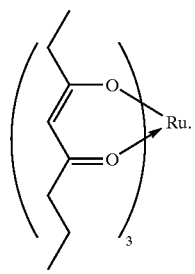

2. A method for producing a CVD material compound, comprising the steps of:

preparing tris (2,4-octa-dionato) ruthenium (III), making said tris (2,4-octa-dionato) ruthenium (III) adsorbed on an adsorbent including alumina, bringing said adsorbent into contact with a first solvent to elute the trans isomer and then bringing said adsorbent into contact with a second solvent having a polarity higher than that of said first solvent to elute the cis isomer.

3. The method for producing a CVD material compound according to claim 2, wherein said first and second solvents are selected from a group consisting of hexane, cyclohexane, benzene, alcohol, acetone, ethyl acetate and mixtures thereof.

4. A chemical vapor deposition method of a ruthenium or ruthenium compound thin film, wherein the CVD material compound according to claim 1 is vaporized and transported onto a substrate surface where said compound is decomposed to deposit the ruthenium or ruthenium compound thereon.

* * * * *